United States Patent [19]

Peterson

[11] 4,124,622

[45] Nov. 7, 1978

[54] CIS-4,5-DIDEHYDRO-12,13(E)-DIDEHYDRO-13,14-DIHYDRO-9,10-DIDEHYDRO-9-DEOXY-PGD$_1$ COMPOUNDS

[75] Inventor: David C. Peterson, Portage, Mich.

[73] Assignee: The Upjohn Company, Kalamazoo, Mich.

[21] Appl. No.: 809,348

[22] Filed: Jun. 23, 1977

Related U.S. Application Data

[62] Division of Ser. No. 614,244, Sep. 17, 1975, and Ser. No. 809,248, Jun. 23, 1977, Pat. No. 4,099,014, which is a division of Ser. No. 614,244.

[51] Int. Cl.$^2$ .................................. C07C 127/00
[52] U.S. Cl. ............................ 260/413; 260/408; 260/410; 260/410.5; 260/410.9 R; 562/503; 560/121
[58] Field of Search ............. 560/121; 260/408, 410, 260/410.5, 410.9 R, 413, 514 D

[56] References Cited

U.S. PATENT DOCUMENTS

| 3,878,239 | 4/1975 | Hayashi et al. ............... 260/514 |
| 4,016,184 | 4/1977 | Morton et al. ................ 260/408 |

Primary Examiner—Robert Gerstl
Attorney, Agent, or Firm—Robert A. Armitage

[57] ABSTRACT

Prostaglandin analogs with the following cyclopentane ring structure:

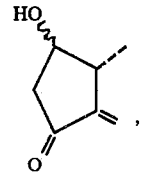

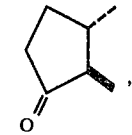

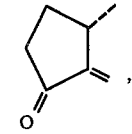

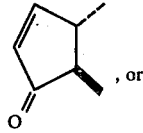

, or

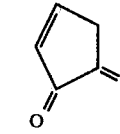

are disclosed along with intermediates useful in their preparation and processes for their preparation. These analogs are useful for some of the same pharmacological purposes as the prostaglandins, particularly and especially as blood platelet aggregation inhibitors.

12 Claims, No Drawings

CIS-4,5-DIDEHYDRO-12,13(E)-DIDEHYDRO-13,14-DIHYDRO-9,10-DIDEHYDRO-9-DEOXY-PGD$_1$ COMPOUNDS

The present application is a divisional application of Ser. No. 614,244, filed Sept. 17, 1975, now pending. U.S. Ser. No. 809,248, filed June 23, 1977, and also a divisional application of Ser. No. 614,244, has now issued as U.S. Pat. No. 4,099,014.

The present invention relates to prostaglandin analogs, for which the essential material constituting disclosure therefor is incorporated by reference here from U.S. Pat. No. 4,099,014.

I claim:

1. A prostaglandin analog of the formula

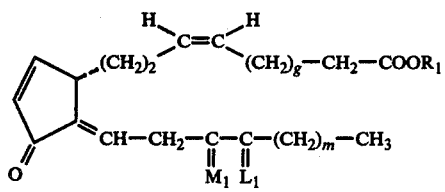

wherein $m$ is 1 to 5, inclusive;
wherein $M_1$ is

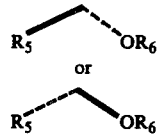

wherein $R_5$ and $R_6$ are hydrogen or methyl, with the proviso that one of $R_5$ and $R_6$ is methyl only when the other is hydrogen;
wherein $L_1$ is

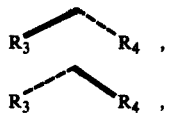

or a mixture of

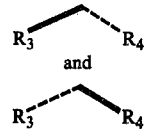

wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of 1 to 3 carbon atoms, inclusive, or a pharmacologically acceptable cation; and
wherein $g$ is one, 2 or 3.

2. A compound according to claim 1, wherein $M_1$ is

3. A compound according to claim 1, wherein $M_1$ is

4. A compound according to claim 3, wherein m is 3.
5. A compound according to claim 4, wherein g is 3.
6. 2a,2b-Dihomo-cis-4,5-didehydro-13,14-dihydro-12,13(E)-didehydro-9-deoxy-9,10-didehydro-PGD$_1$, a compound according to claim 5.
7. A compound according to claim 4, wherein $g$ is 1.
8. A compound according to claim 7, wherein $R_5$ and $R_6$ are both hydrogen.
9. A compound according to claim 8, wherein $R_3$ and $R_4$ are both hydrogen.
10. cis-4,5-Didehydro-13,14-dihydro-12,13(E)-didehydro-9-deoxy-9,10-didehydro-PGD$_1$, a compound according to claim 9.
11. A compound according to claim 8, wherein $R_3$ and $R_4$ are both fluoro.
12. 16,16-Difluoro-cis-4,5-didehydro-13,14-dihydro-12,13(E)-didehydro-9-deoxy-9,10-didehydro-PGD$_1$, a compound according to claim 11.

* * * * *